(12) United States Patent
Mori et al.

(10) Patent No.: US 6,444,985 B1
(45) Date of Patent: Sep. 3, 2002

(54) STABLE ISOTOPE MEASUREMENT METHOD AND APPARATUS BY SPECTROSCOPY

(75) Inventors: Masaaki Mori, Osaka; Yasuhiro Kubo, Shiga; Kazunori Tsutsui, Osaka, all of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/341,045

(22) PCT Filed: Jan. 12, 1998

(86) PCT No.: PCT/JP98/00097
§ 371 (c)(1),
(2), (4) Date: Jul. 1, 1999

(87) PCT Pub. No.: WO98/30888
PCT Pub. Date: Jul. 16, 1998

(30) Foreign Application Priority Data

| Jan. 14, 1997 | (JP) | ............................................. 9-004844 |
| Jan. 14, 1997 | (JP) | ............................................. 9-004845 |

(51) Int. Cl.$^7$ ............................................. G01N 21/35
(52) U.S. Cl. ................................................. 250/339.13
(58) Field of Search ................................... 250/339.13

(56) References Cited

U.S. PATENT DOCUMENTS

| 4,829,183 A | 5/1989 | McClatchie et al. |
| 5,146,294 A | 9/1992 | Grisar et al. |
| 5,486,699 A | 1/1996 | Fabinski et al. ............ 250/345 |
| 5,591,975 A | 1/1997 | Jack et al. |
| 5,747,809 A | * 5/1998 | Eckstrom ..................... 250/345 |

FOREIGN PATENT DOCUMENTS

| EP | 0 584 897 | 3/1994 |
| JP | 61-42219 | 9/1986 |
| JP | 61-42220 | 9/1986 |
| JP | 62-261032 | 11/1987 |
| JP | 5-296922 | 11/1993 |
| JP | 9 166546 | 6/1997 |

* cited by examiner

*Primary Examiner*—Constantine Hannaher
(74) *Attorney, Agent, or Firm*—Finnegan, Henderson, Farabow, Garrett & Dunner LLP

(57) ABSTRACT

A test gas sample containing carbon dioxide $^{13}CO_2$ as a component gas is introduced into a cell, then the absorbance of light transmitted therethrough at a wavelength suitable for the component gas $^{13}CO_2$ is determined, and the concentration of the component gas is determined on the basis of a calibration curve prepared through measurement on test gas samples each containing the component gas in a known concentration. Further, the concentration of water vapor contained in the test gas sample is measured, and the concentration of the component gas in the test gas sample is corrected in accordance with the measured water vapor concentration on the basis of a correction curve prepared through measurement on the test gas samples each containing water vapor in a known concentration (FIG. 4). With the spectrometry, the concentration ratio of the component gas can precisely be determined and corrected by measuring the moisture content in the test gas sample.

5 Claims, 5 Drawing Sheets

F I G. 1
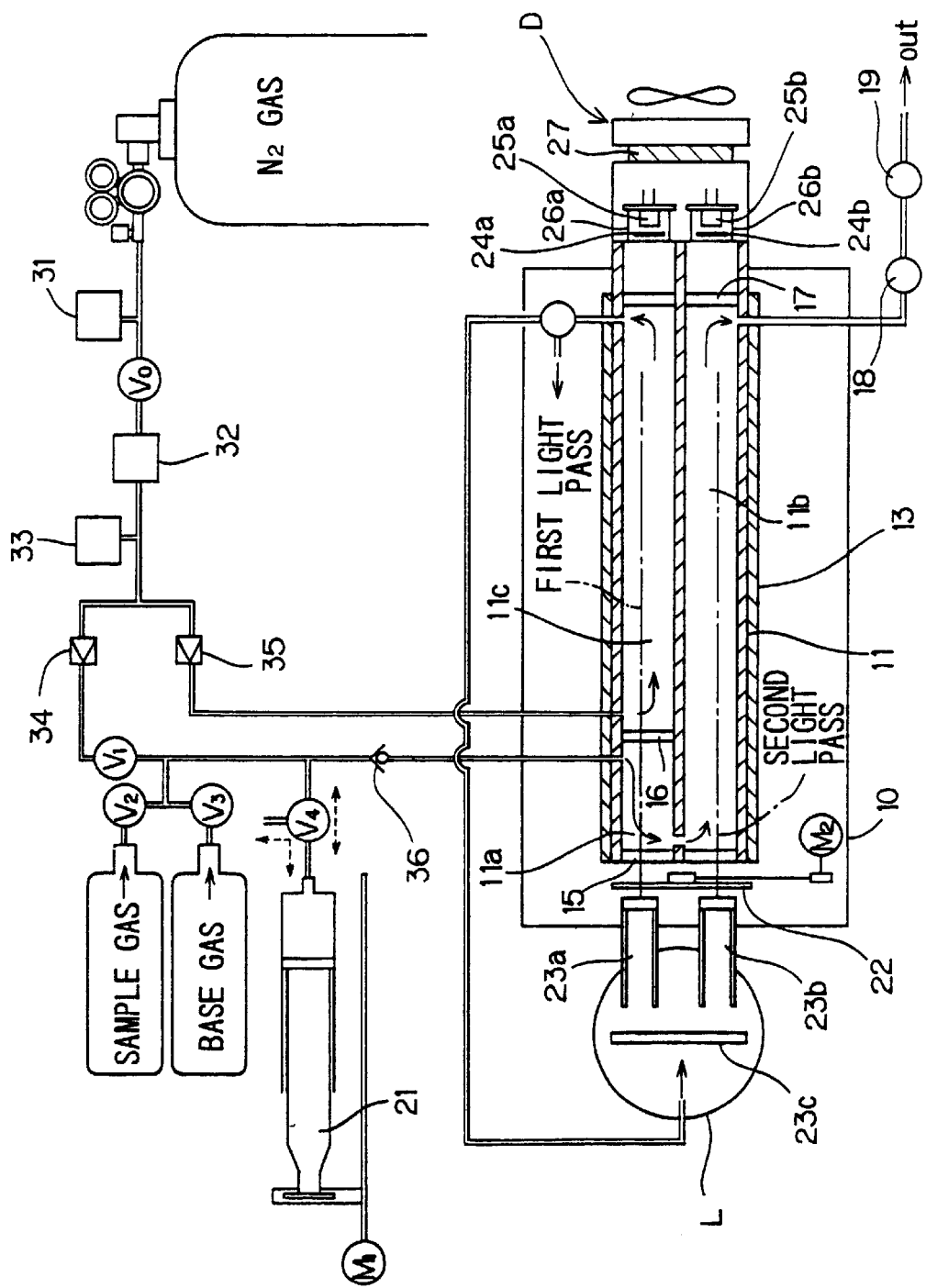

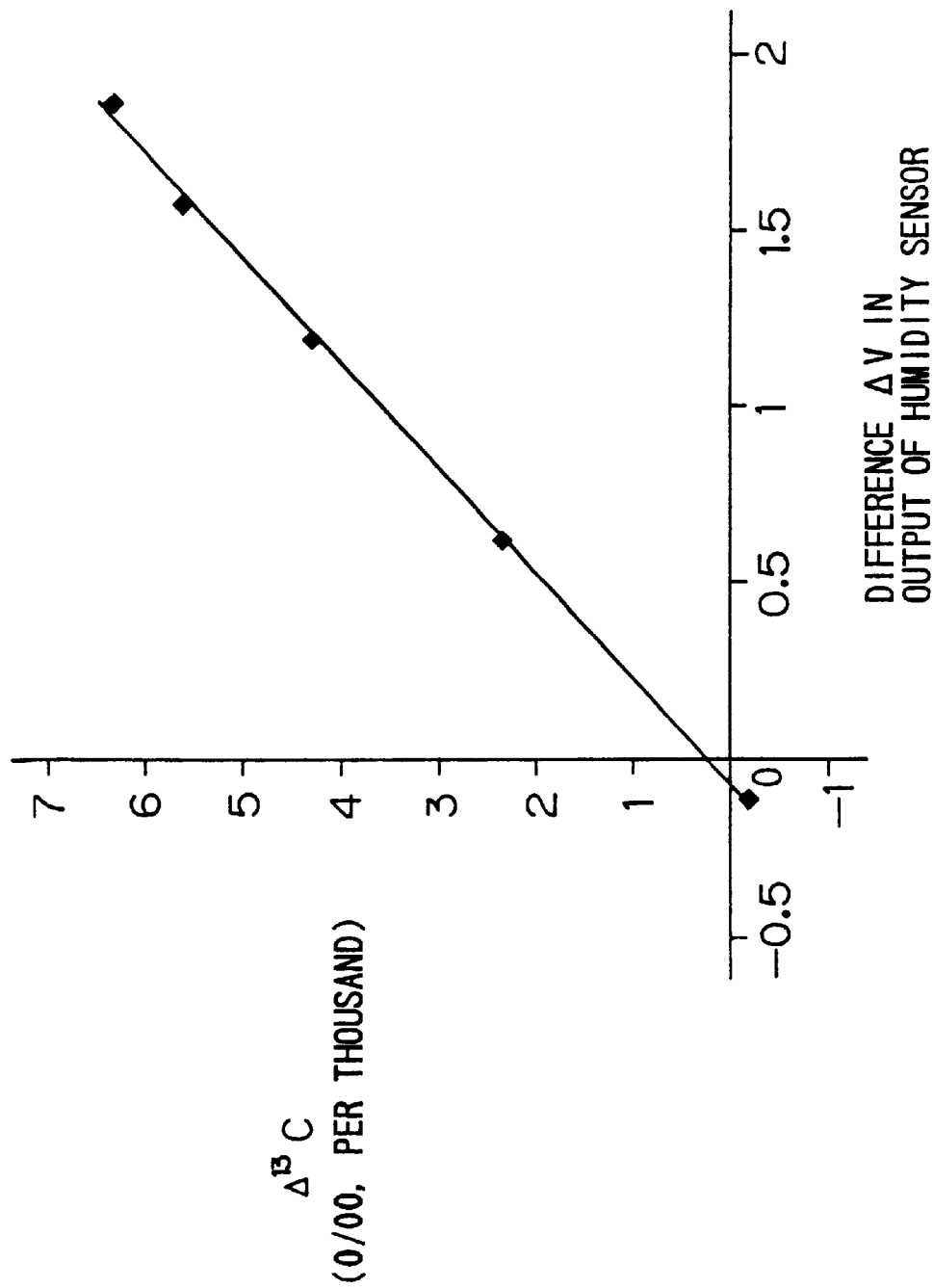

STABLE ISOTOPE MEASUREMENT METHOD AND APPARATUS BY SPECTROSCOPY

TECHNICAL FIELD OF THE INVENTION

Isotopic analyses are useful for diagnosis of a disease in a medical application, in which metabolic functions of a living body can be determined by measuring a change in the concentration or concentration ratio of an isotope after administration of a drug containing the isotope. In the other fields, the isotopic analyses are used for studies on the photosynthesis and metabolism of plants, and for ecological tracing in a geochemical application.

The present invention relates to stable isotope measurement methods and apparatus for spectrometrically measuring the concentration or concentration ratio of an isotopic gas on the basis of the light absorption characteristics of the isotope.

BACKGROUND ART

It is generally known that gastric ulcer and gastritis are caused by bacteria called helicobacter pylori (HP) as well as by a stress.

If the HP is present in the stomach of a patient, an antibiotic or the like should be administered to the patient for bacteria removal treatment. Therefore, it is indispensable to check if the patient has the HP. The HP has a strong urease activity for decomposing urea into carbon dioxide and ammonia.

Carbon has isotopes having mass numbers of 12, 13 and 14, among which $^{13}C$ having a mass number of 13 is easy to handle because of its non-radioactivity and stability.

If the concentration of $^{13}CO_2$ as a final metabolic product or the concentration ratio of $^{13}CO_2$ to $^{12}CO_2$ in breath of a patient is successfully measured after urea labeled with the isotope $^{13}C$ is administered to the patient, the presence of the HP can be confirmed.

However, the concentration ratio of $^{13}CO_2$ to $^{12}CO_2$ in naturally occurring carbon dioxide is 1:100. Therefore, it is difficult to determine the concentration ratio in the breath of the patient with high accuracy.

There have been known methods for determining the concentration ratio of $^{13}CO_2$ to $^{12}CO_2$ by way of infrared spectroscopy (see Japanese Examined Patent Publications No. 61-42219 (1986) and No. 61-42220 (1986)).

In the method disclosed in Japanese Examined Patent Publication No. 61-42220, two cells respectively having a long path and a short path are provided, the path lengths of which are adjusted such that the light absorption by $^{13}CO_2$ in one cell is equal to the light absorption by $^{12}CO_2$ in the other cell. Light beams transmitted through the two cells are led to the detectors, in which the light intensities are measured at wavelengths which ensure the maximum sensitivity. In accordance with this method, the light absorption ratio for the concentration ratio of $^{13}CO_2$ to $^{12}CO_2$ in naturally occurring carbon dioxide can be adjusted to 1. If the concentration ratio is changed, the light absorption ratio also changes by the amount of a change in the concentration ratio. Thus, the change in the concentration ratio can be determined by measuring the change in the light absorption ratio.

DISCLOSURE OF THE INVENTION

A. However, the method for determining the concentration ratio according to the aforesaid literature suffers from the following drawback.

Calibration curves for determining the concentrations of $^{12}CO_2$ and $^{13}CO_2$ should be prepared by using gas samples each having a known $^{12}CO_2$ concentration and gas samples each having a known $^{13}CO_2$ concentration.

To prepare the calibration curve for the $^{12}CO_2$ concentration, the $^{12}CO_2$ absorbances are measured for different $^{12}CO_2$ concentrations. The $^{12}CO_2$ concentrations and the $^{12}CO_2$ absorbances are plotted as abscissa and ordinate, respectively, and the calibration curve is determined by the method of least squares.

The calibration curve for the $^{13}CO_2$ concentration is prepared in the same manner as described above.

The $^{13}CO_2$ concentration or the $^{13}CO_2$ concentration ratio (which is herein meant by $^{13}CO_2$ concentration/$^{12}CO_2$ concentration) in the breath as a test gas sample is typically determined by way of infrared spectroscopy. In this case, since a test sample gas, or breath is exhaled from a living body as a result of the metabolism, the breath contains water vapor in a concentration proximate to saturation.

In the infrared spectroscopy, the absorption of infrared radiation with a particular wavelength by a test gas sample is utilized for determination of the absorbance for the test gas sample.

FIG. 5 is a graph obtained by plotting the measured values of the $^{13}CO_2$ concentration ratio changes with respect to the humidities of test gas samples having different humidities ranging from 0 to 100% wherein the $^{13}CO_2$ concentration ratio with respect to a 0%-humidity gas sample is used as a reference gas sample.

As can be seen from the graph, the measured values of the $^{13}CO_2$ concentration ratio are not the same, but vary depending on the humidity.

Therefore, if the $^{13}CO_2$ concentration or the $^{13}CO_2$ concentration ratio of a test gas sample containing moisture is measured in ignorance of this fact, the measured value is apparently greater than the true value.

One approach to this problem is to remove the moisture contained in the breath sample as the test gas sample through molecular sieving or with the use of a moisture absorbent such as magnesium perchlorate prior to the measurement. However, some problems may be encountered in this approach since the approach requires a large space for housing the moisture absorbent, there is no means for checking if the moisture is completely removed by the moisture absorbent, and the moisture absorbent should periodically be replaced with a new one.

It is, therefore, an object of the present invention to provide a stable isotope measurement method and apparatus for spectrometrically analyzing an isotopic gas, wherein a test gas sample containing carbon dioxide $^{13}CO_2$ as a component gas is introduced into a cell and the concentration or concentration ratio of the component gas is precisely measured and corrected by measuring moisture content in the test gas sample.

A stable isotope measurement method for spectrometrically analyzing an isotopic gas in accordance with the present invention comprises: a first step of introducing a test gas sample into a cell and determining the absorbance of light transmitted therethrough at a wavelength suitable for the component gas $^{13}CO_2$; a second step of determining a concentration of the component gas in the test gas sample on the basis of a calibration curve prepared through measurement on test gas samples each containing the component gas in a known concentration; and a third step of measuring a concentration of water vapor contained in the test gas sample and correcting a concentration of the component gas contained in the test gas sample in accordance with the measured water vapor concentration on the basis of a correction curve prepared through measurement on test gas samples each containing water vapor in a known concentration.

A stable isotope measurement method for spectrometrically analyzing an isotopic gas in accordance with the present invention comprises: a first step of introducing a test gas sample containing carbon dioxide $^{13}CO_2$ and carbon dioxide $^{13}CO_2$ as component gases into a cell and determining the absorbances of light transmitted therethrough at wavelengths suitable for the respective component gases; a second step of determining a concentration ratio between the component gases in the test gas sample on the basis of a calibration curve prepared through measurement on test gas samples each containing the component gases in known concentrations; and a third step of measuring a concentration of water vapor contained in the test gas sample and correcting a concentration ratio between the component gases contained in the test gas sample in accordance with the measured water vapor concentration on the basis of a correction curve prepared through measurement on test gas samples each containing water vapor in a known concentration.

When compared with the prior art method, each of the aforesaid methods additionally include the third step in which the concentration ratio of the component gas is corrected in accordance with the measured water vapor concentration on the basis of the correction curve prepared through the measurement on the test gas samples each containing water vapor in a known concentration.

Although the concentration of the component gas should basically be represented by a single true value, the measured value of the concentration of the component gas varies depending on the water vapor concentration. In view of this fact, the aforesaid methods improve the measurement accuracy of the concentration ratio of the component gas.

The water vapor concentration may otherwise be determined by means of any of various humidity sensors, or may be calculated from the absorbance determined spectrometrically on the basis of the water molecule spectrum. spectrometrically analyzed, the concentration ratio of the component gas is corrected in accordance with the water vapor concentration in the test gas sample. Therefore, the concentration ratio of the component gas can be determined with a higher accuracy.

B. In the infrared spectrometric analysis, the $^{12}CO_2$ concentration in a breath sample obtained before the drug administration is calculated from the measured $^{12}CO_2$ absorbance on the basis of a $^{12}CO_2$ calibration curve, while the $^{13}CO_2$ concentration in the breath sample is calculated from the measured $^{13}CO_2$ absorbance on the basis of a $^{13}CO_2$ calibration curve. The $^{12}CO_2$ and $^{13}CO_2$ concentrations in the breath sample obtained after the drug administration are determined in the same manner.

If the $CO_2$ concentrations in the two breath samples are substantially the same, it is possible to use narrower ranges of the $^{12}CO_2$ calibration curve and the $^{13}CO_2$ calibration curve. Thus, the measurement accuracy can be improved by using limited ranges of the calibration curves.

For equalization of the $CO_2$ concentrations in the two breath samples, either one of the breath samples should be diluted. Typically used as a gas for dilution (hereinafter referred to as "diluent gas") is nitrogen gas which exhibits no absorption in the infrared region of the radiation spectrum (nitrogen gas is used as the diluent gas in the embodiment of the invention disclosed in Japanese Unexamined Patent Publication No. 9-1665546 (1997) which was filed prior to the present invention).

In this dilution method, however, the diluted breath sample has a different component gas ratio from the undiluted breath sample, because diluent gas contains only nitrogen but breath sample contains oxygen, moisture and etc. as well as nitrogen.

As a result, the difference in the component gas ratio influences the determination of the $^{13}CO_2$ concentration and the concentration ratios between $^{12}CO_2$ and $^{13}CO_2$, so that the measured values may be erroneous.

It is, therefore, another object of the present invention to provide a method for spectrometrically analyzing an isotopic gas, wherein a breath sample as a test gas sample containing a plurality of component gases is introduced into a cell and the concentrations of the component gases are precisely measured through spectrometry by diluting the test gas sample in such a manner that the component gas composition in the test gas sample is not changed.

To achieve this object, there is provided a stable isotope measurement method for spectrometrically analyzing an isotopic gas, wherein two test gas samples are sampled from a single subject and, if the $CO_2$ concentration of one of the test gas samples is higher than the $CO_2$ concentration of the isotopic gas, and the following automatic control is performed. other test gas sample, the one test gas sample is diluted with air (atmospheric air) to a $CO_2$ concentration level which is equivalent to that of the other test gas sample for measurement of the concentration ratios $^{13}CO_2/^{12}CO_2$ in the respective test gas samples (claim 5).

In this method, the two breath samples are analyzed on condition that the breath samples have the same $CO_2$ concentration level. This makes it possible to use limited ranges of the calibration curves. In addition, the component gas composition in the breath sample is not changed by the dilution because air is used as the diluent gas. As a result, the measurement accuracy can be improved.

Methods according to present claims 6 and 7 each provide a more specific procedure for the method for spectrometrically analyzing the isotopic gas in accordance with claim 5, and are each based on the precondition that a first test gas sample is first filled in a single cell for measurement of the intensity of light transmitted therethrough and, after the first test gas sample is discharged from the cell, a second test gas sample is filled in the cell for measurement of the intensity of light transmitted therethrough.

As described above, the $CO_2$ concentrations in the two test gas samples can be generally equalized by diluting either one of the two test gas samples so as not to change the component gas composition of the breath sample. This makes it possible to use limited ranges of the $^{12}CO_2$ and $^{13}CO_2$ calibration curves. The accuracy of the calibration curves is increased as the ranges of the calibration curves to be used are narrowed. Therefore, the measurement accuracy can be improved by limiting the ranges of the calibration curves to be used.

DESCRIPTION OF DRAWINGS

FIGS. 2A and 2C are diagrams illustrating gas flow paths to be employed when a cell is cleaned by passing a clean reference gas therethrough. FIG. 2B is a diagram illustrating gas flow path to be employed when a base gas is sucked into a gas injector 21 from a breath sampling bag and then mechanically pushed out into the gas flow path at a constant rate. FIG. 2D is a diagram illustrating a gas flow path to be employed when a sample gas is sucked into the gas injector 21 from a breath sampling bag and then mechanically pushed out into the gas flow path at a constant rate.

FIGS. 3A and 3D are diagrams illustrating gas flow paths to be employed when a cell is cleaned by passing a clean reference gas therethrough. FIG. 3B–1 is a diagram illustrating a gas flow path to be employed when a predetermined amount of the reference gas is sucked into the gas injector 21. FIG. 3B–2 is a diagram illustrating a gas flow path to be employed when a predetermined amount of air is sucked into the gas injector 21 with a three-way valve V4 opened to the atmospheric air. FIG. 3C is a diagram illustrating a gas flow path to be employed when a base gas is sucked into the gas injector 21 from a breath sampling bag and then mechanically pushed out into the gas flow path at a constant rate. FIG. 3E is a diagram illustrating a gas flow path to be employed when a sample gas is sucked into the gas injector 21 from a breath sampling bag and is mechanically injected into the gas flow path at a constant rate.

FIG. 4 is a graph prepared in such a manner that sample gases having different humidities and a base gas having a humidity of 0% were prepared by mixing a $CO_2$ gas having a predetermined $^{13}CO_2$ concentration and containing no moisture and a $CO_2$ gas having the predetermined $^{13}CO_2$ concentration and containing moisture, and differences $\Delta V$ between an output value for the humidity of the base gas and output values for the humidities of the sample gases detected by a humidity sensor 19 and differences between the $^{13}CO_2$ concentration ratio in the base gas and the $^{13}CO_2$ concentration ratios in the sample gases determined on the basis of a calibration curve were plotted as abscissa and ordinate, respectively.

DESCRIPTION OF CARRYING OUT THE INVENTION

With reference to the attached drawings, embodiments of the present invention will hereinafter be described which are adapted for a case where the $^{13}CO_2$ concentration ratio in a breath sample is spectrometrically determined after administration of an urea diagnostic drug labeled with an isotope $^{13}C$.

I. Breath Sampling Test

Before the urea diagnostic drug is administered to a patient, breath of the patient is collected in a breath sampling bag. The volume of the breath sampling bag is about 250 ml. Then, the urea diagnostic drug is orally administered to the patient and, after a lapse of 10 to 15 minutes, breath of the patient is collected in another breath sampling bag in the same manner as in the previous breath sampling.

The breath sampling bags obtained before and after the drug administration are respectively attached to predetermined nozzles of an apparatus for spectrometrically analyzing an

II. Apparatus for Spectrometrically Analyzing Isotopic Gas

Figure 3A:
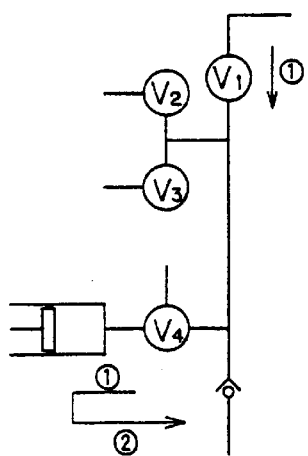
FIGS. 3A to 3E are diagrams illustrating gas flow paths in the apparatus for spectrometrically analyzing the isotopic gas. Particularly.
Figures 1, 3B:
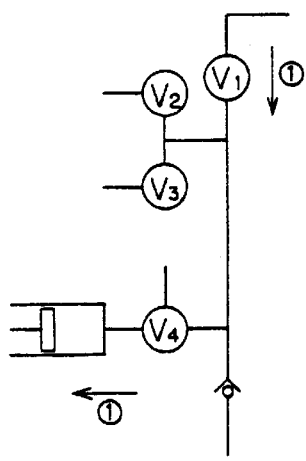
FIG. 1 is a block diagram illustrating the overall construction of an apparatus for spectrometrically analyzing an isotopic gas.

FIG. 1 is a block diagram illustrating the overall construction of the apparatus for spectrometrically analyzing the isotopic gas.

The breath sampling bag containing the breath sample collected after the drug administration (hereinafter referred to as "sample gas") and the breath sampling bag containing the breath sample collected before the drug administration (hereinafter referred to as "base gas") are respectively attached to the predetermined nozzles of the apparatus. The breath sampling bag containing the base gas is connected to a valve V3 through a resin or metal pipe (hereinafter referred to simply as "pipe"), while the breath sampling bag containing the sample gas is connected to a valve V2 through a pipe.

A reference gas (any gas exhibiting no absorption at a wavelength for measurement, e.g., nitrogen gas) is supplied from a gas tank to the apparatus. The reference gas flows through a pressure release valve 31, a valve V0, a regulator 32 and a flow meter 33, and is diverged into a reference cell 11c through a needle valve 35 and into a first sample cell 11a for measuring the $^{12}CO_2$ absorbance through a valve V1 and a check valve 36.

A gas injector 21 (volume: 70 cm$^3$) for quantitatively injecting the sample gas or the base gas is connected to a flow path between the valve V1 and the first sample cell 11a via a three-way valve V4. The gas injector 21 is a syringe-like device having a piston and a cylinder. The piston is driven by cooperation of a motor M1, a feed screw connected to the motor M1 and a nut fixed to the piston.

As shown in FIG. 1, a cell chamber 11 has the first sample cell 11a having a shorter length for measuring a $^{12}C_2$ absorbance, a second shorter cell 11b having a longer length for measuring a $^{13}CO_2$ absorbance, and the reference cell 11c through which the reference gas is passed. The first sample cell 11a communicates with the second sample cell 11b. Gas is introduced into the first sample cell 11a and then into the second sample cell 11b, and discharged therefrom. The reference gas is introduced into the reference cell 11c. Then, a portion of the reference gas flows into a case 10 housing the cell chamber 11 and discharged therefrom, and the other portion of the reference gas flows into an infrared radiation source device L and discharged therefrom. Specifically, the first and second sample cells 11a and 11b have lengths of 13 mm and 250 mm, respectively, and the reference cell 11c has a length of 236 mm.

A discharge pipe extending from the second sample cell 11b is provided with an $O_2$ sensor 18 and a humidity sensor 19. Usable as the $O_2$ sensor 18 are commercially available oxygen sensors, for example, a solid electrolyte gas sensor such as a zirconia sensor and an electrochemical gas sensor such as a galvanic cell sensor. Usable as the humidity sensor 19 are commercially available sensors such as utilizing a porous ceramic resistor and a polymer resistor.

The infrared radiation source device L has two waveguides 23a and 23b for guiding an infrared beam. The generation of the infrared radiation may be achieved arbitrarily, for example, a ceramic heater. (surface temperature: 450° C.) and the like can be used. A rotary chopper 22 for periodically blocking and passing the infrared beams is provided adjacent to the infrared radiation source device L. A light path along which an infrared beam emitted from the infrared radiation source device L is transmitted though the first sample cell 11a and the reference cell 11c is herein referred to as "first light path", while a light path along which an infrared beam is transmitted through the second sample cell 11b is herein referred to as "second light path".

A reference character D denotes an infrared beam detector for detecting the infrared beams transmitted through the cells. The infrared beam detector D has a first interference filter 24a and a first detection element 25a disposed in the first light path, and a second interference filter 24b and a second detection element 25b disposed in the second light path.

The first interference filter 24a (band width: about 20 nm) transmits infrared radiation having a interference of about 4,280 nm for measurement of the $^{12}CO_2$ absorbance. The second interference filter 24b (band width: about 50 nm) transmits infrared radiation having a wavelength of about 4,412 nm for measurement of the $^{13}CO_2$ absorbance. Usable as the first and second detection elements 25a and 25b are any elements capable of detecting infrared radiation, for example, a semiconductor infrared sensor such as of PbSe.

The first interference filter 24a and the first detection element 25a are housed in a package 26a filled with an inert gas such as Ar. Similarly, the second interference filter 24b and the second detection element 25b are housed in a package 26b filled with an inert gas.

The whole infrared beam detector D is maintained at a constant temperature (25° C.) by means of a heater and a Peltier element 27. The detection elements in the packages 26a and 26b are kept at 0° C. by means of a Peltier element.

The cell chamber 11 is formed of a stainless steel, and vertically or laterally sandwiched between heaters 13.

The cell chamber 11 has two tiers. The first sample cell 11a and the reference cell 11c are disposed in one tier, and the second sample cell 11b is disposed in the other tier, The first light path extends through the first sample cell 11a and the reference cell 11c which are disposed in series, and the second light path extends through the second sample cell 11b. Reference characters 15, 16 and 17 denote sapphire transmission windows through which the infrared radiation is transmitted.

The cell chamber 11 is kept at a constant temperature (40° C.) by controlling the heaters 13.

III. Measuring Procedure

In the measurement, the $CO_2$ concentrations of the base gas and the sample gas are adjusted to substantially the same level. For this purpose, the $CO_2$ concentrations of the base gas and the sample gas are measured in a preliminary measurement. If the preliminarily measured $CO_2$ concentration of the base gas is higher than the preliminarily measured $CO_2$ concentration of the sample gas, the $CO_2$ concentration of the base gas is measured after the base gas is diluted to a $CO_2$ concentration level equivalent to that of the sample gas, and then the $CO_2$ concentration of the sample gas is measured in a main measurement.

If, in the main measurement, the preliminarily measured $CO_2$ concentration of the base gas is lower than the preliminarily measured $CO_2$ concentration of the sample gas, the $CO_2$ concentration of the base gas is measured as it is, and the $CO_2$ concentration of the sample gas is measured after the sample gas is diluted to a $CO_2$ concentration level equivalent to that of the base gas.

The measuring procedure includes reference gas measurement, preliminary base gas measurement, reference gas measurement, preliminary sample gas measurement, reference gas measurement, base gas measurement, reference gas measurement, sample gas measurement and reference gas measurement which are to be performed in this order.

III-1. Preliminary Base Gas Measurement

The gas flow path and the cell chamber 11 in the apparatus for spectrometrically analyzing the isotopic gas are cleaned by passing the clean reference gas therethrough, and a reference light intensity is measured.

Figure 2A:
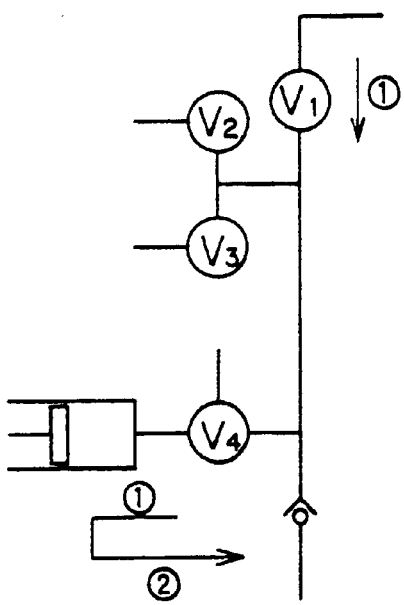
FIGS. 2A to 2D are diagrams illustrating gas flow paths in the apparatus for spectrometrically analyzing the isotopic gas. Particularly.

More specifically, the reference gas is sucked into the gas injector 21 with the three-way valve V4 opened to the side of the cell chamber 11 and with the valve V1 opened as shown in FIG. 2A, and then mechanically pushed out into the flow path from the gas injector 21 with the valve V1 closed to clean the first sample cell 11a and the second sample cell 11b. The reference gas is constantly passed through the reference cell 11c.

Figure 2B:
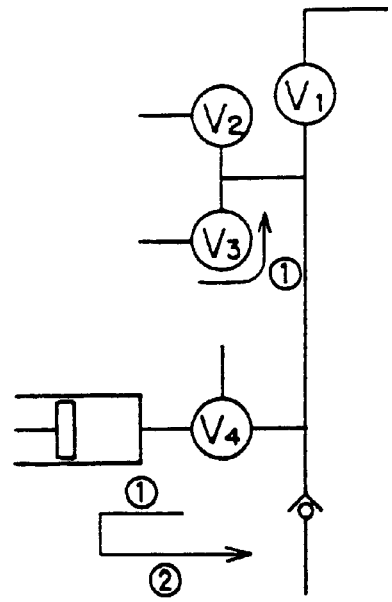

In turn, the base gas is sucked into the gas injector 21 from the breath sampling bag with the valve V3 opened as shown in FIG. 2B, and then mechanically pushed out into the flow path from the gas injector 21 at a constant flow rate. At this time, the intensity of light transmitted through the base gas is measured by means of the detection elements 25a and 25b, and the $CO_2$ concentration of the base gas is determined from its absorbance on the basis of a calibration curve.

III-2. Preliminary Sample Gas Measurement

The gas flow path and the cell chamber 11 in the apparatus for spectrometrically analyzing the isotopic gas are cleaned by passing the clean reference gas therethrough, and a reference light intensity is measured.

Figure 2C:
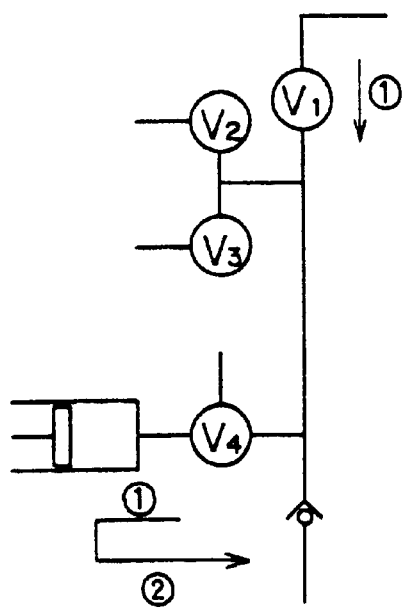

More specifically, the reference gas is sucked into the gas injector 21 with the valve V1 opened as shown in FIG. 2C, and then pushed out into the flow path from the gas injector 21 with the valve V1 closed to clean the first sample cell 11a and the second sample cell 11b.

Figure 2D:
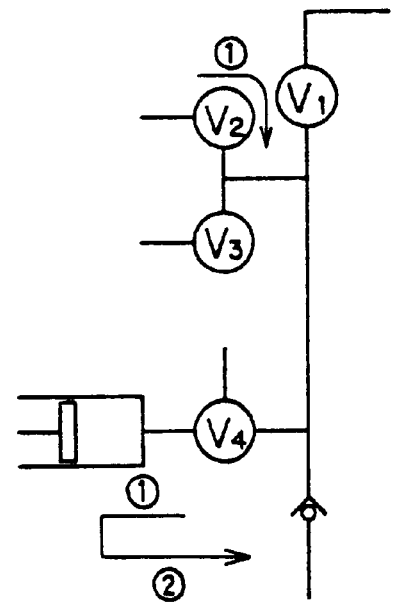

In turn, the sample gas is sucked into the gas injector 21 from the breath sampling bag with the valve V2 opened as shown in FIG. 2D, and then mechanically pushed out into the flow path from the gas injector 21 at a constant flow rate. At this time, the intensity of light transmitted through the sample gas is measured by means of the detection elements 25a and 25b, and the $CO_2$ concentration of the sample gas is determined from its absorbance on the basis of the calibration curve.

III-3. Reference Measurement

The gas flow path is changed, and then the reference gas is passed therethrough to clean the gas flow path and the cell chamber 11. After a lapse of about 30 seconds, light intensities are measured by means of each of the detection elements 25a and 25b.

More specifically, the reference gas is sucked into the gas injector 21 with the valve V1 opened as shown in FIG. 3A, and then pushed out into the flow path from the gas injector 21 with the valve V1 closed to clean the first sample cell 11a and the second sample cell 11b. At this time, the intensities of light transmitted through the reference gas are measured by means of the detection element 25a and the detection element 25b. The light intensities thus obtained by the first and second detection elements 25a and 25b are represented by $^{12}R_1$ and $^{13}R_1$, respectively.

III-4. Base Gas Measurement

The $CO_2$ concentration of the base gas obtained by the first detection element 25a in "III-1. Preliminary base gas measurement" is compared with the $CO_2$ concentration of the sample gas obtained by the first detection element 25a in "III-2. Preliminary sample gas measurement". If the $CO_2$ concentration of the base gas is higher than the $CO_2$ concentration of the sample gas, the base gas is diluted with the air or reference gas in the gas injector 21 to a $CO_2$ concentration level equivalent to that of the sample gas, and then the light intensity measurement is performed on the base gas thus diluted.

More specifically, a predetermined amount of the reference gas is sucked into the gas injector 21 with the valve V1 opened as shown in FIG. 3B–1. In turn, the base gas is sucked into the gas injector 21 with the valve V3 opened as shown in FIG. 3C, and mixed with the reference gas. Since the $CO_2$ concentrations of the two breath samples are adjusted to substantially the same level by thus diluting the base gas with the reference gas, the ranges of the $^{12}CO_2$ and $^{13}CO_2$ calibration curves to be used can be narrowed.

Figures 2, 3B:
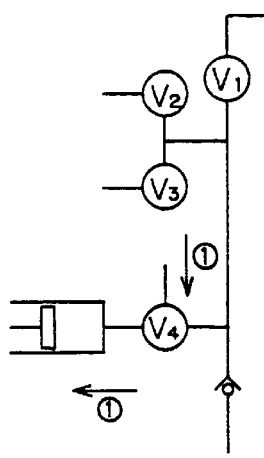
Figure 3C:
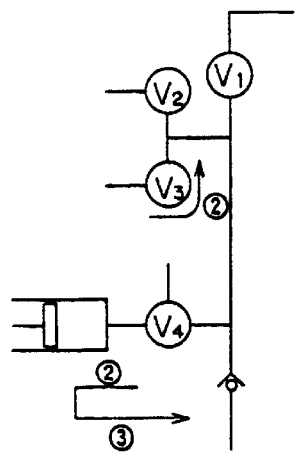

Alternatively, a predetermined amount of air may be sucked into the gas injector 21 with the three-way valve V4 opened to the atmospheric air as shown in FIG. 3B–2. In turn, the base gas is sucked into the gas injector 21 with the three-way valve V4 opened to the cell chamber and with the valve V3 opened as shown in FIG. 3C, and then mixed with the air.

Since the $CO_2$ concentrations of the two breath samples are adjusted to substantially the same level by thus diluting the base gas with the air, the ranges of the $^{12}CO_2$ and $^{13}CO_2$ calibration curves to be used can be narrowed.

It should be noted that the measuring procedure employing the dilution method shown in FIG. 3B–2 is characterized in that the $CO_2$ concentrations of the two breath samples are adjusted to substantially the same level, and does not necessarily require to employ a step of constantly maintaining the $CO_2$ concentration at a constant level as described in Japanese Examined Patent Publication No. 4-124141 (1992). The use of limited ranges of the calibration curves can be achieved simply by adjusting the $CO_2$ concentrations of the base gas and the sample gas to substantially the same level. Since the $CO_2$ concentrations of the base gas and the sample gas may vary within a range of 1% to 6% in actual measurement, it is very troublesome to always maintain the $CO_2$ concentrations at a constant level.

If the $CO_2$ concentration of the base gas is lower than the $CO_2$ concentration of the sample gas, the base gas is not diluted, but the base gas is subjected to the measurement as it is.

The base gas is mechanically pushed out into the flow path from the gas injector 21 at a constant flow rate and, at this time, light intensity measurement is performed by means of the detection elements 25a and 25b.

The light intensities thus obtained by the first and second detection elements 25a and 25b are represented by $^{12}B$ and $^{13}B$, respectively.

III-5. Reference Measurement

Figure 3D:
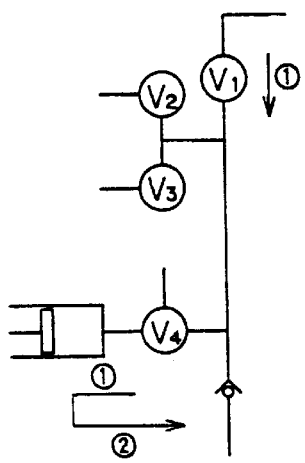

The cleaning of the gas flow path and the cells and the light intensity measurement on the reference gas are performed again by employing the flow path shown in FIG. 3D.

The light intensities thus obtained by the first and second detection elements 25a and 25b are represented by $^{12}R_2$ and $^{13}R_2$, respectively.

III-6. Sample Gas Measurement

Figure 3E:
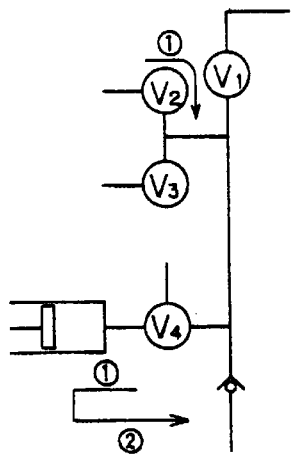
Figure 5:
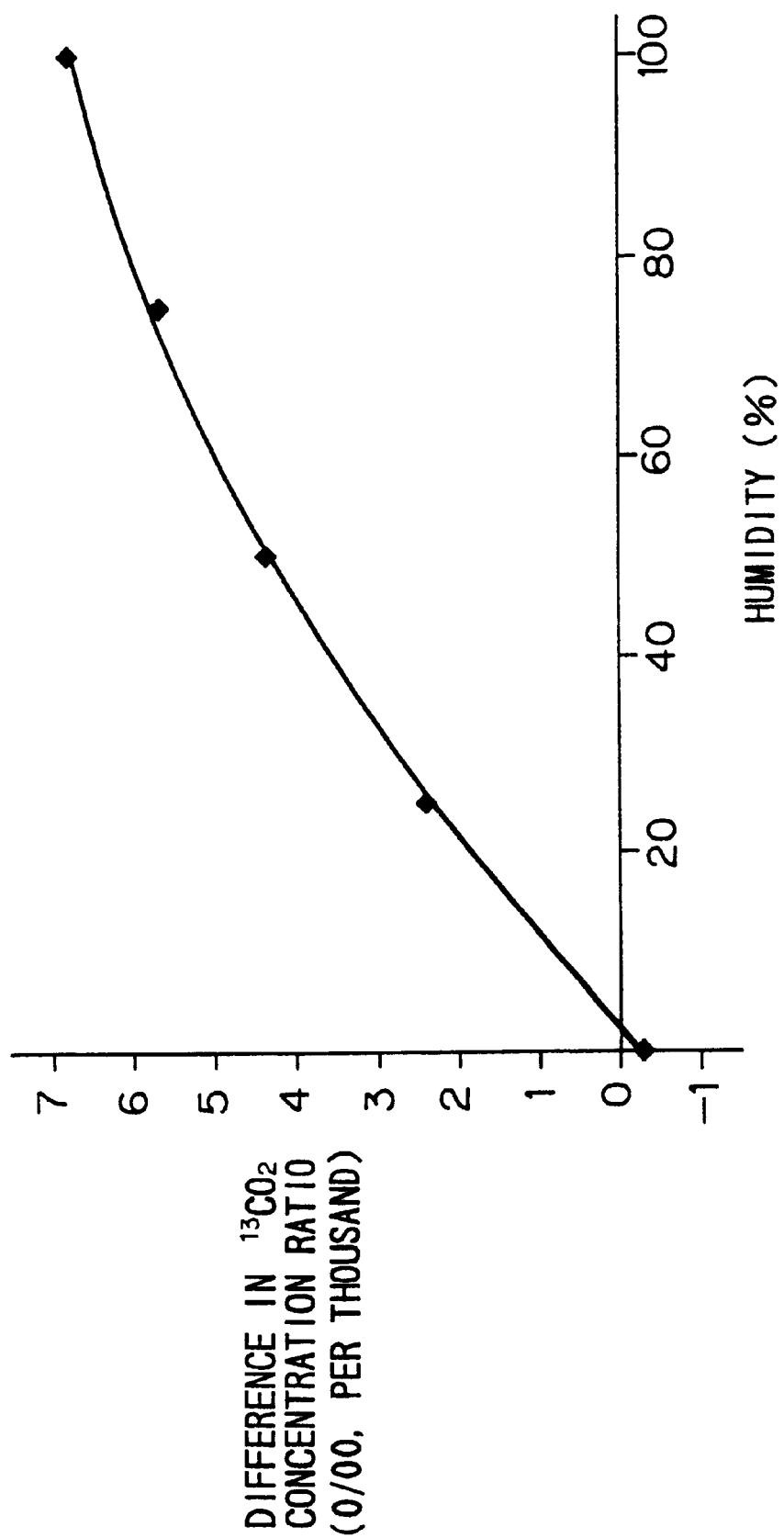
FIG. 5 is a graph illustrating a relationship between the humidity and the $^{13}CO_2$ concentration ratio for the sample gas having different humidities.

If the base gas is diluted in "III-4. Base gas measurement", the sample gas is sucked into the gas injector 21 from the breath sampling bag as shown in FIG. 3E, and then mechanically pushed out into the flow path from the gas injector 21 at a constant flow rate. At this time, light intensities are measured by the detection elements 25a and 25b.

If the base gas is not diluted in "III-4. Base gas measurement", the sample gas is diluted with the reference gas or air to a $CO_2$ concentration level equivalent to that of the base gas in the gas injector 21, and then the intensities of light transmitted through the sample gas is measured by means of the detection elements 25a and 25b.

The light intensities thus obtained by the first and second detection elements 25a and 25b are represented by $^{12}S$ and $^{13}S$, respectively.

III-7. Reference Gas Measurement

The cleaning of the gas flow path and the cells and the light intensity measurement on the reference gas are performed again.

The light intensities thus obtained by the first and second detection elements 25a and 25b are represented by $^{12}R_3$ and $^{13}R_3$, respectively.

IV. Data Processing

IV-1. Calculation of Absorbances of Base Gas

The $^{12}CO_2$ absorbance $^{12}Abs(B)$ and the $^{13}CO_2$ absorbance $^{13}Abs(B)$ of the base gas are calculated on the basis of the transmitted light intensities $^{12}R_1$ and $^{13}R_1$ for the reference gas, the transmitted light intensities $^{12}B$ and $^{13}B$ for the base gas and the transmitted light intensities $^{12}R_2$ and $^{13}R_2$ for the reference gas obtained in accordance with the aforesaid measuring procedure.

The $^{12}CO_2$ absorbance $^{12}Abs(B)$ is calculated from the following equation:

$$^{12}Abs(B) = -\log[2 \times {}^{12}B/({}^{12}R_1 + {}^{12}R_2)]$$

The $^{13}CO_2$ absorbance $^{13}Abs(B)$ is calculated from the following equation:

$$^{13}Abs(B) = -\log[2 \times {}^{13}B/({}^{13}R_1 + {}^{13}R_2)]$$

Since the calculation of the absorbances is based on the light intensities obtained in the base gas measurement and the averages $(R_1+R_2)/2$ of the light intensities obtained in the reference measurements performed before and after the base gas measurement, the influence of a drift (a time-related influence on the measurement) can be eliminated. Therefore, when the apparatus is turned on, there is no need for waiting until the apparatus reaches a complete thermal equilibrium (it usually takes several hours), so that the measurement can be started immediately after the turn-on of the apparatus.

IV-2. Calculation of Absorbances of Sample Gas

The $^{12}CO_2$ absorbance $^{12}Abs(S)$ and the $^{13}CO_2$ absorbance $^{13}Abs(S)$ of the sample gas are calculated on the basis of the transmitted light intensities $^{12}R_2$ and $^{13}R_2$ for the reference gas, the transmitted light intensities $^{12}S$ and $^{13}S$ for the sample gas and the transmitted light intensities $^{12}R_3$ and $^{13}R_3$ for the reference gas obtained in accordance with the aforesaid measuring procedure.

The $^{12}CO_2$ absorbance $^{12}Abs(S)$ is calculated from the following equation:

$$^{12}Abs(S) = -\log[2 \times {}^{12}S/({}^{12}R_2 + {}^{12}R_3)]$$

The $^{13}CO_2$ absorbance $^{13}Abs(S)$ is calculated from the following equation:

$$^{13}Abs(S) = -\log[2 \times {}^{13}S/({}^{13}R_2 + {}^{13}R_3)]$$

Since the calculation of the absorbances is based on the light intensities obtained in the sample gas measurement and the averages of the light intensities obtained in the reference measurements performed before and after the sample gas measurement, the influence of a drift can be eliminated.

IV-3. Calculation of Concentrations

The $^{12}CO_2$ concentration and the $^{13}CO_2$ concentration are calculated by using calibration curves.

The calibration curves are prepared on the basis of measurement performed by using test gas samples of known $^{12}CO_2$ concentrations and test gas samples of known $^{13}CO_2$ concentrations.

For preparation of the calibration curve for $^{12}CO_2$, the $^{12}CO_2$ absorbances for different $^{12}CO_2$ concentrations ranging from about 0.5% to about 6% are measured. The $^{12}CO_2$ concentrations and the $^{12}CO_2$ absorbances are plotted as abscissa and ordinate, respectively, and an approximate curve is determined by the method of least squares. An approximate quadratic curve, which includes relatively small errors, is employed as the calibration curve in this embodiment.

For preparation of the calibration curve for $^{13}CO_2$, the $^{13}CO_2$ absorbances for different $^{13}CO_2$ concentrations ranging from about 0.006% to about 0.07% are measured. The $^{13}CO_2$ concentrations and the $^{13}CO_2$ absorbances are plotted as abscissa and ordinate, respectively, and an approximate curve is determined by the method of least squares. An approximate quadratic curve, which includes relatively small errors, is employed as the calibration curve in this embodiment.

Strictly speaking, the $^{13}CO_2$ absorbance determined by individually measuring a gas sample containing $^{12}CO_2$ and a gas sample containing $^{13}CO_2$ may be different from the $^{13}CO_2$ absorbance determined by measuring a gas sample containing both $^{12}CO_2$ and $^{13}CO_2$. This is because the interference filters each have a certain bandwidth and the $^{12}CO_2$ absorption spectrum partially overlaps the $^{13}CO_2$ absorption spectrum. Since gas samples containing both $^{12}CO_2$ and $^{13}CO_2$ are to be analyzed in this measurement method, the overlap of these spectra should be corrected in determination of the calibration curves. The calibration curves to be employed in this measurement are corrected for the overlap of the absorption spectra.

The $^{12}CO_2$ concentration and $^{13}CO_2$ concentration of the base gas and the $^{12}CO_2$ concentration and $^{13}CO_2$ concentration of the sample gas determined by using the aforesaid calibration curves are represented by $^{12}Conc(B)$, $^{13}Conc(B)$, $^{12}Conc(S)$ and $^{13}Conc(S)$, respectively.

IV-4. Calculation of Concentration Ratios

The concentration ratio of $^{13}CO_2$ to $^{12}CO_2$ is determined. The concentration ratios in the base gas and in the sample gas are expressed as $^{13}Conc(B)/^{12}Conc(B)$ and $^{13}Conc(S)/^{12}Conc(S)$, respectively.

Alternatively, the concentration ratios in the base gas and in the sample gas may be defined as $^{13}Conc(B)/[^{12}Conc(B)+^{13}Conc(B)]$ and $^{13}Conc(S)/[^{12}Conc(S)+^{13}Conc(S)]$, respectively. Since the $^{12}CO_2$ concentration is much higher than the $^{13}CO_2$ concentration, the concentration ratios expressed in the former way and in the latter way are substantially the same.

IV-5. Determination of $^{13}C$ Change

A $^{13}C$ difference between the sample gas and the base gas is calculated from the following equation:

$\Delta^{13}C$=[Concentration ratio of sample gas−Concentration ratio of base gas]×$10^3$/Concentration ratio of base gas (Unit: per mill (per thousand))

IV-6. Correction of $^{13}C$ Change

The difference $\Delta^{13}C$ in the $^{13}CO_2$ concentration ratio between the base gas and the sample gas is subjected to a correction for water vapor concentration (correction for humidity) according to the present invention.

For this purpose, the difference $\Delta^{13}C$ in the $^{13}CO_2$ concentration ratio is corrected with the use of a graph prepared by plotting difference $\Delta^{13}C$ in the $^{13}CO_2$ concentration ratios with respect to outputs of the humidity sensor 19.

More specifically, the preparation of the graph is achieved in the following manner. A 3% $CO_2/N_2$ balance gas having a humidity of 0% is filled in two gas sampling bags, and water vapor is charged to saturation into one of the gas sampling bag for preparation of a 3% $CO_2/N_2$ balance gas having a humidity of 100%. By mixing these two gases, five sample gases having different humidities ranging from 0% to 100% and a base gas having a humidity of 0% is prepared. An output of the humidity sensor 19 indicative of the humidity of the base gas and outputs of the humidity sensor 19 indicative of the humidities of the sample gases are obtained. The differences $\Delta V$ between the output for the base gas and the outputs for the sample gases are plotted as abscissa. Since the humidity of the base gas is 0%, the differences $\Delta V$ in the output correspond to values indicative of the humidities of the sample gases. Then, the differences in the $^{13}CO_2$ concentration between the base gas and the sample gases are plotted as ordinate. Thus, the preparation of the graph is completed.

Experimentally obtained values are shown in Table 1.

TABLE 1

| Humidity of sample gas (%) | Sensor output of base gas | Sensor output of sample gas | Difference in sensor output | Difference in $^{13}CO_2$ concentration ratio (0/00) |
| --- | --- | --- | --- | --- |
| 0 | 1.653168 | 4.541812 | −0.111356 | −0.2 |
| 25 | 1.789176 | 2.407378 | 0.618202 | 2.34 |
| 50 | 1.925964 | 3.117390 | 1.191426 | 4.28 |
| 75 | 2.022190 | 3.594348 | 1.572158 | 5.60 |
| 100 | 2.110666 | 3.970968 | 1.860302 | 6.32 |

Although the outputs of the sensor indicative of the humidity of the base gas should basically be the same level, the measured output values varied with a drift. This is because the response speed of the humidity sensor 19 was problematic and the measurement was performed before the humidity sensor 19 did not reach complete equilibrium. The values in Table 1 are plotted as shown in a graph of FIG. 4.

The differences $\Delta^{13}C$ in the $^{13}CO_2$ concentration ratio between the base gas and the sample gases are corrected on the basis of the graph and the differences in the output of the humidity sensor 19 between the base gas and the sample gases.

What is claimed is:

1. A stable isotope measurement method for spectrometrically analyzing an isotopic gas by introducing a test gas sample containing a component gas into a cell, measuring an intensity of light transmitted therethrough at a wavelength suitable for the component gas, and processing data of the light intensity to determine a concentration of the component gas, the test gas sample being human breath, the component gas being carbon dioxide $^{13}CO_2$, where the wavelength suitable for the component gas is about 4412 nm, the method comprising:

a first step of introducing the test gas sample into the cell and determining an absorbance of light transmitted therethrough at the wavelength suitable for the component gas;

a second step of determining a concentration of the component gas in the test gas sample on the basis of a calibration curve prepared through measurement on gas samples each containing the component gas in a known concentration; and a third step of measuring a concentration of water vapor contained in the test gas sample and correcting the concentration of the component gas in the test gas sample in accordance with the measured water vapor concentration on the basis of a correction curve prepared through measurement on gas samples each containing water vapor in a known concentration.

2. A stable isotope measurement method for spectrometrically analyzing an isotopic gas by introducing a test gas sample containing a plurality of component gases into a cell, measuring intensities of light transmitted therethrough at wavelengths suitable for the respective component gases, and processing data of the light intensities to determine a concentration ratio between the component gases, the test gas sample being human breath, the component gases being carbon dioxide $^{12}CO_2$ and carbon dioxide $^{13}CO_2$, where the wavelength suitable for $^{12}CO_2$ is about 4280 nm, and the wavelength suitable for $^{13}CO_2$ is about 4412 nm, the method comprising:

- a first step of introducing the test gas sample into the cell and determining absorbances of light transmitted therethrough at the wavelengths suitable for the respective component gases;
- a second step of determining a concentration ratio between the component gases in the test gas sample on the basis of a calibration curve prepared through measurement on gas samples each containing the component gases in known concentrations; and
- a third step of measuring a concentration of water vapor contained in the test gas sample and correcting the concentration ratio between the component gases in the test gas sample in accordance with the measured water vapor concentration on the basis of a correction curve prepared through measurement on gas samples each containing water vapor in a known concentration.

3. A stable isotope measurement method for spectrometrically analyzing an isotopic gas as set forth in claim 2, wherein:

the correction curve in the third step is prepared by determining absorbances at the wavelengths suitable for the respective component gases for the plurality of gas samples containing water vapor in different concentrations, then determining concentrations of or concentration ratios between the respective component gases in the gas samples on the basis of the calibration curve, and plotting ratios or differences between the concentrations of or the concentration ratios between the respective component gases in the gas samples thus determined with respect to the water vapor concentrations of the gas samples, and the correction in the third step is achieved by obtaining a concentration correction value or a concentration ratio correction value for the component gases by fitting the water vapor concentration of the test gas sample obtained in the third step to the correction curve, and then dividing the concentrations of or the concentration ratio between the respective component gases in the test gas sample obtained in the second step by the concentration correction value or the concentration ratio correction value obtained on the basis of the correction curve, or subtracting the concentration correction value or the concentration ratio correction value from the concentrations of or the concentration ratio between the respective component gases in the test gas sample.

4. A stable isotope measurement apparatus for spectrometrically analyzing an isotopic gas by introducing a test gas sample containing a plurality of component gases into a cell, measuring intensities of light transmitted therethrough at wavelengths suitable for the respective component gases, and processing data of the measured light intensities by data processing means to determine a concentration ratio between the component gases, wherein the test sample is human breath, the component gases are carbon dioxide $^{12}CO_2$ and carbon dioxide $^{13}CO_2$, comprising:

- a first filter for passing light the wavelength of which suitable for $^{12}CO_2$ is about 4280 nm, and a second filter for passing light the wavelength of which suitable for $^{13}CO_2$ is about 4412 nm,
- absorbance calculation means for determining absorbances of light transmitted through the test gas sample introduced into the cell on the basis of the light intensities measured at the wavelengths suitable for the respective component gases;
- concentration calculation means for calculating a concentration ratio between the component gases in the test gas sample on the basis of a calibration curve prepared through measurement on gas samples each containing the component gases in known concentrations;
- water vapor concentration measuring means for measuring a concentration of water vapor contained in the test gas sample; and
- correction means for correcting the concentration ratio between the component gases in the test gas sample in accordance with the measured water vapor concentration on the basis of a correction curve prepared through measurement on gas samples each containing water vapor in a known concentration.

5. A stable isotope measurement apparatus for spectrometrically analyzing an isotopic gas as set forth in claim 4, wherein the bandwidth of the first filter is about 20 nm, and the bandwidth of the second filter is about 50 nm.

* * * * *